United States Patent [19]

Schulte

[11] Patent Number: 4,717,660

[45] Date of Patent: Jan. 5, 1988

[54] DETECTION OF BACTERIA BY FLUORESCENT STAINING IN AN EXPANDED BUFFY COAT

[75] Inventor: Thomas H. Schulte, Cary, N.C.

[73] Assignee: Becton, Dickinson and Company, Franklin Lakes, N.J.

[21] Appl. No.: 573,988

[22] Filed: Jan. 26, 1984

[51] Int. Cl.$^4$ ............................................. C12Q 1/24
[52] U.S. Cl. ................................. 435/30; 435/29; 435/34
[58] Field of Search ......................... 435/29, 34, 30

[56] References Cited

U.S. PATENT DOCUMENTS

| | | | |
|---|---|---|---|
| 4,027,660 | 6/1977 | Wardlaw et al. | 210/927 |
| 4,190,328 | 3/1980 | Levine et al. | |
| 4,225,669 | 9/1980 | Melnick et al. | 435/29 |
| 4,225,783 | 9/1980 | Palin et al. | 435/29 |
| 4,304,720 | 12/1981 | Dean et al. | 435/29 |
| 4,508,821 | 4/1985 | Mansour et al. | 435/34 |

OTHER PUBLICATIONS

Roser et al.–Chem. Abst., vol. 90 (1980), pp. 234, 429U.
Scholefield–Chem. Abst., vol. 88 (1978), pp. 101, 252f.
Pollard et al.–Chem. Abst., vol. 66 (1967), pp. 113, 248t.
Wardlaw, S. C. and R. A. Levine, Quantitative Buffy Coat Analysis, J. Am. Med. Asso. 249, 617 (1983), p. 620, center col.

Primary Examiner—Sam Rosen
Attorney, Agent, or Firm—Richard E. Brown

[57] ABSTRACT

A method for the detection of microorganisms e.g. bacteria in a blood sample comprises staining the microorganisms with a fluorescent dye and observing the fluorescence emission of an expanded buffy coat. The expanded buffy coat is obtained by centrifuging the stained sample in a hematocrit tube containing a float which occupies most of the buffy coat volume. The expanded buffy coat further separates into sub-layers. Intracellular microorganisms congregate in and are detected in the granulocyte sub-layer. The method may be modified to assess phagocytic activity.

17 Claims, 4 Drawing Figures

U.S. Patent
Jan. 5, 1988
4,717,660
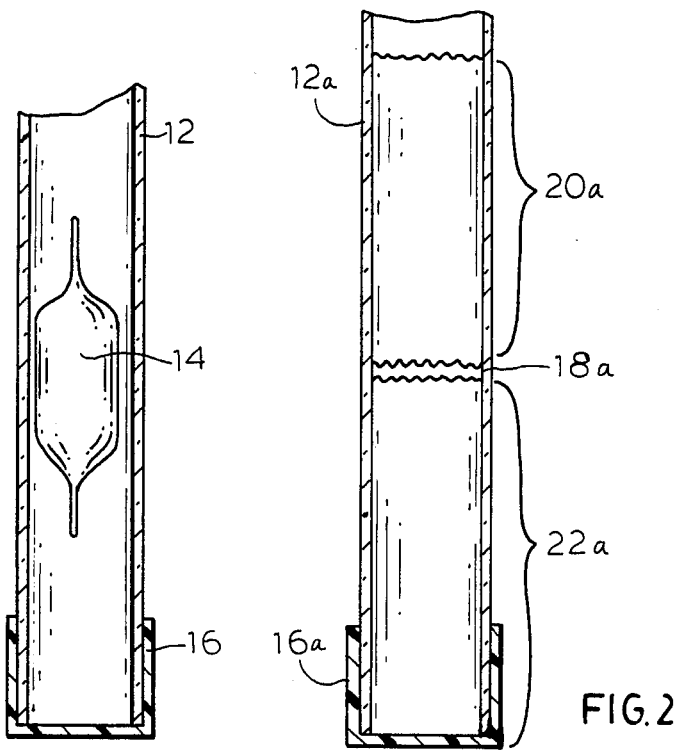
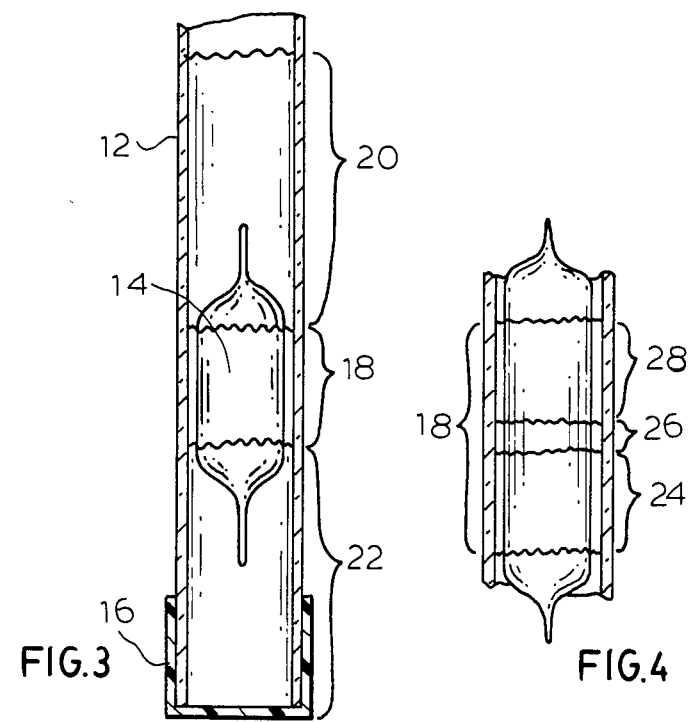
FIG.1  FIG.2  FIG.3  FIG.4

DETECTION OF BACTERIA BY FLUORESCENT STAINING IN AN EXPANDED BUFFY COAT

BACKGROUND

1. Field of the Invention

This invention relates to the detection of microorganisms and the assessment of the phagocytosis of microorganisms. More particularly, it relates to the detection and the assessment of the phagocytosis of microorganisms in a blood sample, wherein the microorganisms are stained with a fluorescent dye and examined in an expanded buffy coat.

2. Description of the Prior Art

Blood is normally a sterile fluid. However, when microorganisms are present, the resulting infections may be life threatening situations. Successful treatment of blood infections requires early diagnosis, and proper treatment cannot be initiated until accurate identification of the pathogen has been accomplished. Identification is rendered very difficult in the early stages of the infection because the concentration of the pathogen in the blood is usually low.

A variety of systems has been proposed for the early detection of microorganisms in the blood. Two procedures are currently in use in hospital microbiology laboratories. One is a conventional blood culturing method wherein a growth medium is inocurlated with the patient's blood and an increase in turbidity, indicative of growth, is monitored over a period of time. This method is the one most utilized, but the length of time required for growth to result in turbidity is a severe disadvantage. In some instances, fastidious organisms may require up to 7 days for detection by turbidity.

The second hospital technique is an automated radioisotope detection method wherein the conversion of radioisotope $^{14}C$-labeled bacterial nutrients to $^{14}C$-labeled $CO_2$ is monitored in the head space gas. This method has been shown to be able to detect 30% of the positive blood cultures in 12 hours and 70% within 24 hours, but is also dependent on bacterial growth for detection. Although detection is accomplished sooner than with the conventional culturing methods, the 12-24 hour period involved is still a serious drawback where rapid detection of the pathogen is important.

Culturing can sometimes be avoided if the microoganisms are concentrated or partially separated from some of the other components in the sample which might mask their presence and thereby hinder detection and subsequent identification. Standard methods for concentrating or separating microorganisms from such samples have relied on specific physical properties, such as size or density. However, use of such techniques is complicated by the fact that different species of microorganisms differ greatly in these physical properties. More recent methods allowing rapid identification include counterimmunoelectrophoresis, latex agglutination and radioimmunologic methods. Such methods, although successful in certain situations, have been much less successful in detection of circulating microorganisms, especially during the early stages of infection.

Other methods for the detection of microorganisms have employed various density gradients to separate the microorganisms from various blood components. Blood cell lysis/ filtration and lysis/centrifugation methods involve the addition of blood cell lysis agents to dispose of the eukaryotic cells and subsequent collection of the microorganisms by either passage through a bacterial retention membrane filter or by centrifugation. Exemplary of these methods is that disclosed in U.S. Pat. No. 4,131,512 to Dorn wherein a lysed blood sample is deposited on a high density liquid cushioning agent and subjected to centrifugation to cause collection of the bacteria at the interface between the cushioning agent and the sample. These methods, however, also require a final step of growing the bacteria on nutrient agar plates for detection by colony formation and thus are subject to the same limitation as direct culturing techniques.

Another method which aids in the isolation of microorganisms utilizes leukocytes. Leukocytes (white blood cells) include lymphocytes, monocytes, and granulocytes, and the term "leukocytes" as used herein referes to one or more of these subclasses.

One of the primary functions of leukocytes is ingestion and destruction of microorganisms invading the peripheral blood. The process of ingestion is known as phagocytosis and microorganisms which have been phagocytized are hereinafter referred to as intracellular bacteria. Microorganisms which have not been phagocytized are referred to as extracellular bacteria.

Phagocytosis is the natural defense mechanism against infection, and clinical microbiology laboratories have often sought to detect infections by visualizing and scoring leukocytes containing intracellular microorganisms. One such method which has achieved some limited success in serious blood infections, such as septicemia, is microscopic examination of smears made from the buffy coat. In this procedure, unclotted blood is centrifuged whereby the buffy coat forms from various blood components, including leukocytes, as a thin layer between the plasma and erythrocyte layers. Microorganisms, if present, are also found in this layer and thus are concentrated and separated from some of the other blood components. Study of the buffy coat has heretofore required transfer from the centrifuge tube to a means of examination, as, for example, a microscope slide. Because of the narrowness of the buffy layer, such transfer has resulted in unavoidable errors.

U.S. Pat. No. 4,027,660 to Wardlow describes expansion of the buffy coat by the addition of a plastic float to a conventional microhematocrit tube wherein the plastic float is of the proper specific gravity so as to become positioned directly above the erythrocyte layer and directly below the plasma layer of a centrifuged blood sample. Thus it occupies the location of the buffy coat. Application of this device to obtain a complete blood cell count is described by Wardlaw et al. (J. Am. Med. Asso. 249, 617 (1983) and a commercial embodiment thereof is marketed (QBC Centrifugal Hematology System, Clay Adams, Division of Becton Dickinson & Co., Parsippany, N.J. Preliminary studies directed toward detection of blood borne parasites are also disclosed by Wardlaw et al.

Buffy coat smears may be stained with a variety of standard agents such as Gram, Wright, Jenner-Giemsa, Leishman, or May-Grunwald-Giemsa stains and visualized under the microscope. Recent studies (A. Kostiala et al., Am. J. Clin. Pathol. 72,437 (1981) have shown that, in rabbits, experimental bacteremias and fungemias induced by inoculations of a variety of pathogens could be detected regularly by microscopy or subculture of the Gram-stained buffy coat when cell populations reached 300-1000/ml. In contrast, Reik et al., J. Am. Med. Asso. 245, 357 (1981) report that bacteria in various samples, including blood, are not visible by Gram stain unless present in concentrations close to $1\times 10^5$ cells/ml. Also, in clinical studies, M. J. Coppen et al., (J. Clin. Pathol. 34, 1375 (1981)) report that buffy coat smears have little practical value for identification of microorganisms because of the high incidence of false positivies and false negatives.

The use of fluorescence microscopy for a variety of purposes is increasing in both clinical and research laboratories, and has been used in a variety of inexpensive staining protocols. For example, ethidium bromide has been used extensively to stain both eukaryotic and prokaryotic cells. Acridine orange (AO) has been utilized to stain bacteria in various clinical samples, including blood (L. R. McCarthy and J. E. Senne, J. Clin. Microb., 11 281 (1980)). G. Krönvall and E. Myhre, (Acta Path. Microb. Scand, 85, 249 (1977)) describe AO staining of intracellular bacteria, but only buccal and traceal samples.

The analysis of phagocytosis has led to the elucidation of many syndromes with genetic or acquired defects in chemotaxis, motility, ingestion or microbial killing. Various methods to study phagocytic activity have been developed. These methods include treatment with agents which lyse extracellular particles while leaving intracellular particles intact, quantitation of the ingestion phase of phagocytosis by use of the electron microscope or radioactive agents, and differential staining of extracellular and intracellular microorganisms with fluorescent dyes. Exemplary of staining methods is that reported by Goldner (Laboratory Medicine, 14, 291 (1983)) wherein AO is used to stain all the microorganisms in a sample, which are counted. Subsequently, a second dye, crystal violet, is used to quench the fluorescence in the external environment, leaving the intracellular microorganisms as the only fluorescing species. A count of extracellular microorganims is obtained by difference.

The above methods require expensive equipment, use of dangerous radioactive agents, or require excessive operator handling. There is a definite need for a better method for the assessment of phagocytic activity in a biological fluid sample.

SUMMARY OF THE INVENTION

The method of the present invention comprises detecting microorganisms in a whole blood sample and assessing phagocytic activity in the sample. Both the extracellular and intracellular microorganisms are stained and differentiated with a single fluorescent dye which stains microorganisms selectively in the presence of blood components. After the sample is stained, it is preferably drawn up into a centrifuge tube provided with a float. The float occupies most of the volume of the tube normally occupied by the buffy coat and thereby results in an expanded buffy coat when the stained sample is centrifuged. The expanded buffy coat itself separates into sublayers termed the platelet, granulocyte, and nongranulocyte layers, and study of these layers may be carried out directly in the centrifuge tube without transfer of the sample into an alternate mode for examination. Intracellular microorganisms are generally found in the granulocyte layer. The fluorescence emission of the granulocyte layer thus provides a method for detection of intracellular microorganisms.

In accordance with this invention, microorganisms in very small blood samples or in samples of low microorganism concentration are detected without a culturing step, thereby greatly decreasing the time required for detection. Microorganisms are detected at much lower concentrations than by use of known buffy coat analyses because the microorganisms are concentrated in a buffy coat sublayer and because enhanced staining selectivity and sensitivity are achieved relative to known staining methods, such as Gram stain.

By appropriate modifications within the purview of one skilled in the art, the method is adapted to provide a method for assessment of the ability of leukocytes to ingest microorganisms.

BRIEF DESCRIPTION OF THE DRAWINGS

FIG. 1 is a side elevational view of a typical tube and float which may be used in the method of the invention;

FIG. 2 is a side elevational view of a typical tube without a float after centrifugation of a blood sample;

FIG. 3 is a side elevational view of the tube and float of FIG. 1 after centrifugation of a blood sample; and FIG. 4 is an enlarged side view of the buffy coat section of the tube of FIG. 1 after centrifugation of a blood sample.

DETAILED DESCRIPTION OF THE INVENTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

According to the procedure of this invention, intracellular microorganisms in a blood sample are selectively stained with a fluorescent dye and thereby visualized. Most microorganisms are stained under the principles of this invention, as, for example, but not limited to *S. aureus, E. coli, Strep. fecalis, S. epidermidis, Proteus mirabilis, P. aeruginosa, Bacteroides fragilis, Klebsiella pneumoniae, H. influenza* and *N. meningitidis.*

Although it is understood that the invention will be practiced on a fluid sample, such as blood, which may or may not contain microorganisms, the invention is best demonstrated by a model system wherein a suitable sample fluid is inoculated with externally grown microorganisms. The microorganisms can be grown in any suitable medium as for example, trypticase soy broth, and removed during the log growth phase. A quantity of cells, from about $10^4$ to $10^8$, preferably about $10^6$, is washed with saline, suspended in normal saline, and the suspension mixed thoroughly with the sample fluid in a ratio of 1 volume parts of cell suspension and from about 5 to about 50 volume parts of sample. Preferably a 10 volume percent suspension is used. Sample fluids which may be used are whole blood or whole blood pre-treated with a suitable anticoagulant, preferably heparin. Exemplary of other anticoagulants which may be used are ethylenediamine tetraacetic acid and sodium polyanethol sulfonate (hereinafter referred to as EDTA and SDS, respectively), although it is understood by those skilled in the art that EDTA and SDS inhibit phagocytosis and thus cannot be used in a model system as described above. These anticoagulants may be used with a patient's blood sample, because phagocytosis will have occured before the sample was drawn.

The mixture of cells and sample fluid is incubated for from about 10 minutes to about 2 hours, preferably about 30 minutes, to allow the leukocytes and microorganisms to become associated. The temperature of incubation may be from ambient to about 50° C., preferably from about 37° C. to about 42° C. Alternatively, the staining may be done without prior incubation. It is understood that, when using a patient's blood sample, an incubation step is unnecessary and the sample may be stained directly.

Any fluorescent dye may be used which selectively stains microorganisms, including intracellular microorganisms, in the presence of blood components. Exemplary of a variety of dyes which may be used are thioflavin T, DAPI and, preferably, ethidium bromide.

Staining is preferably carried out in the presence of an aqueous staining buffer. A preferred staining buffer comprises sodium borate, EDTA, formaldehyde and a surface active agent such as Triton-X-100. The buffered mixture is treated with the fluorescent dye. The amount of dye to be added will be determined by the microorganisms and the sample being used, and in general, the final concentration of dye may be varied from about 1 to about 1000 ug per ml of final volume, preferably from about 10 to about 50 ug/ml. Preferably, the dye is added as an aqueous solution, preferably of from 0.001 to 0.01 percent by weight. All percentages used herein are by weight, unless otherwise indicated. The ratio of sample to buffer to dye is, preferably, 7 parts:2 parts:1 part by volume, however, it is clear to one skilled in the art that any suitable ratio may be used.

When using the preferred dye of the invention, ethidium bromide, the intracellular microorganisms accept the stain almost immediately, and staining is completed by the conclusion of the centrifugation period. In contrast, blood components such as platelets and erythrocytes do not stain at all. The nuclei of the leukocytes stain slowly and begin to fluoresce within 10 to 20 minutes after addition of dye.

After staining, the sample is drawn into a centrifuge tube, preferably a microhematocrit tube, containing a float. FIG. 1 shows the preferred tube of the invention to include a capillary tube 12, a float 14 and a closure 16. Both tube 12 and float 14 preferably are circular in cross section. The inside diameter of tube 12 typically is from about 0.5 to about 10 mm., preferably from about 1.2 to about 1.6 mm. The outside diameter of float 14 is from about 0.45 to about 6, preferably from about 1.1 to about 1.5 mm. The float thus occupies from about 50 to about 95 percent, preferably from about 88 to about 92 percent of the cross-sectional area of the tube. The specific gravity of float 14 may be from about 1.03 to about 1.09, preferably from about 1.05 to 1.06. Closure 16 may be of any suitable design and may be attached to the end of tube 12 by any suitable means. Preferably tube 12 is inserted into closure 16 by an interference fit.

In use, staining buffer and staining solution are added to the sample fluid suspected to contain microorganisms. The sample is drawn into the tube, closure 16 is affixed to tube 12, and float 14 is inserted. Centrifugation is carried out at a rotation rate and for a time period suitable to cause maximum separation of the buffy coat layer. A time period of from about 5 to 20 min., preferably about 10 minutes, and a rotation rate of from about 8000 to about 15,000 rpm, preferably about 10,500 rpm are usually optimum.

For purposes of comparison of the present invention to the prior art tubes, FIG. 2 shows a typical appearance of a tube 12a after centrifugation of a blood sample without insertion of a float. A buffy coat, 18a, appears as a narrow band between a plasma layer 20a and an erythrocyte layer 22a. FIG. 3, on the other hand, shows a typical appearance of the tube 12 after centrifugation of a blood sample with float 14 wherein a buffy coat 18 is expanded by float 14. Buffy coat 18 is expanded in comparison to buffy coat 18a by a factor of from about 5 to about 12. When float 14 is of the preferred shape, size and specific gravity, the preferred expansion factor is 9 to 11.

When the buffy coat assumes its expanded shape due to the presence of the float, separation of the expanded buffy coat into sub-layers takes place. FIG. 4 shows separation of the expanded buffy coat 18 into a granulocyte layer 24, a non-granulocyte layer 26 and a platelet layer 28.

After centrifugation, the sub-layers 24, 26 and 28, respectively, of the expanded buffy coat are examined for fluorescence emission. For this examination, the sub-layers may be removed from the tube and transferred to a microscope slide, or, preferably, the examination may be made directly on the sample in the tube. The wavelength of the light used for excitation depends on the dye used. When the dye used is ethidium bromide, the slide or tube is preferably observed using emitted light above 580 nm after excitation of the sample at 515 nm.

Analysis may also be carried out by fluorescence activated flow cytometry. This procedure is particularly advantageous when the microorganisms are present at low levels. In this procedure, cells are passed, substantially one at a time, through the focused beam of a light source whereby they are caused to emit fluorescent signals which are detected. In the present invention, the buffy coat sub-layers are suspended in saline and passed through the beam at a rate of from about 0.01 ml./min. to about 0.20 ml./min, preferably about 0.1 ml/min.

When the invention is to be used for assessment of phagocytic function, practice of the invention is carried out in accordance with the detailed description herein given wherein microorganisms are added to the patient's blood sample. After the incubation, staining and centrifugation steps, the fluorescence emission of the granulocyte and non-granulocyte layers are determined. If properly functioning leukocytes are present, the granulocyte layer will fluoresce due to the presence of intracellular microorganisms. If phagocytic dysfunction is present, there will be little or no fluorescence emission in the granulocyte layer. A method to study the rate of phagocytosis is also provided by the invention by staining and examining the sublayers of the expanded buffy coat after various times of incubation.

The following examples are provided to further illustrate the invention but are not to be construed in any way as limiting the scope of the invention.

EXAMPLE 1

To each of 6 microfuge tubes was added 15 ul each of ethidium bromide solution and an aqueous staining buffer solution consisting of 40 mM sodium borate, 24 mM EDTA, 0.02% formaldehyde and 0.02% Triton-x-100. After mixing, 120 ul of EDTA endocarditic rabbit blood was added to 3 of the tubes and 120 ul of EDTA control rabbit blood was added to the other 3 tubes. After mixing, the samples were drawn up into empty microhematocrit tubes, floats, similar to the float of FIG. 1, of specific gravity 1.055 were added, the bottoms of the tubes were capped, and the tubes were centrifuged for 5 min. The tubes were examined under a 10× fluorescence-objective on a microscope. Few fluorescent cells were present in any layer with the control blood. An intense band of fluorescent cells was present in the granulocyte layer with the infected blood.

EXAMPLE 2

The procedure of Example 1 was repeated except acridine orange was used instead of ethidium bromide. Observation revealed many fluorescent cells principally green and orange with some pink and yellow, in all tubes in all layers, including the platelet and erythrocyte layers. This experiment with acridine orange gave no clear indication of differences between control and infected rabbit blood because acridine orange stains blood components as well as bacteria.

EXAMPLE 3

Nine microfuge tubes were divided into 3 groups of 3 tubes each, and the 3 tubes in each group were charged as follows:
TUBE 1—50 ul normal saline
TUBE 2—50 ul E. coil suspension ($2.8 \times 10^6$ cells/ml.)
TUBE 3—50 ul S. aureus suspension ($1.2 \times 10^7$ cells/ml.)
Heparinized human blood (350 ul) was added to each tube, and the three groups of tubes were incubated at 37° C. as follows:
Group 1—15 min.
Group 2—30 min.
Group 3—60 min.

After incubation, the tubes were treated with 50 ul each of ethidium bromide solution and the staining buffer of example 1. The samples were drawn up into microhematocrit tubes, floats of specific gravity 1.055 were added to each tube, and centrifugation of all tubes for 5 min. was carried out. The tubes were examined with a fluorescence microscope. Fluorescent cells were seen in the granulocyte layer in all tubes to which microorganisms had been added. The tubes which had been incubated for longer periods showed greater numbers of cells in the granulocyte layers because phagocytosis had proceeded further.

With increasing time after addition of the stain, leukocyte nuclei began to fluoresce. However, the tubes to which microorganisms has been added consistently had more fluorescent cells than the control tubes, and the S. aureus tubes had more fluorescent cells than the E. coli tubes.

In summary, the invention is an improved method for detection of microorganisms in a blood sample. After staining the microorganisms, the sample is centrifuged in a hematocrit tube containing a float, which causes the buffy coat to expand and separate into sub-layers. Intracellular microorganisms are found in the granulocyte sub-layer, and may be detected by the fluorescence emission of this layer. Suitable modification of the method provides a method to study phagocytosis.

What is claimed is:

1. A method for the detection of bacteria in a blood sample comprising staining bacteria in a blood sample with ethidium bromide, centrifuging said sample in a hematocrit tube containing a float to cause formation of an expanded buffy coat and whereby the bacteria are concentrated in a buffy coat sublayer and then detecting said bacteria by applying excitation light to said expanded buffy coat and observing fluorescence emission from said expanded buffy coat.

2. The method in accordance with claim 1 wherein said blood sample is treated with an anticoagulant before said staining.

3. The method in accordance with claim 2 wherein said anticoagulant is selected from the group consisting of heparin, ethylenediamine tetraacetic acid and sodium polyanethol sulfonate.

4. The method in accordance with claim 1 wherein said hematocrit tube is a microhematocrit tube.

5. The method in accordance with claim 1 wherein said float has a specific gravity of from about 1.03 to about 1.09.

6. The method in accordance with claim 1 wherein said expanded buffy coat separates into granulocyte, non-granulocyte and platelet sub-layers.

7. The method in accordance with claim 6 wherein intracellular bacteria are detected in said granulocyte sub-layer.

8. A method for the detection of bacteria in a blood sample comprising staining bacteria in a blood sample with a fluorescent dye which selectively stains bacteria in the presence of blood components, centrifuging said sample in a tube to cause formation of an expanded buffy coat and whereby the bacteria are concentrated in a buffy coat sublayer in said tube and then detecting said bacteria by examination of said expanded buffy coat.

9. The method in accordance with claim 8 wherein said dye is selected from the group consisting of thioflavin T, DAPI and ethidium bromide.

10. A method for the detection of bacteria in a whole blood sample comprising the steps of:
(a) treating a whole blood sample with an anticoagulant, a staining buffer and ethidium bromide to provide a mixture;
(b) drawing said mixture into a microhematocrit tube containing a float;
(c) centrifuging said mixture whereby a buffy coat is formed and whereby the bacteria are concentrated in the buffy coat sublayer and said buffy coat is expanded by said float and thereby separated into platelet, granulocyte and non-granulocyte sub-layers; and
(d) detecting bacteria in said sub-layers of said sample by applying excitation light to said sub-layers and detecting fluorescence emission of said ethidium bromide in said sub-layers.

11. The method in accordance with claim 10 wherein intracellular bacteria are detected in said granulocyte sub-layer.

12. The method in accordance with claim 10 wherein said staining buffer comprises sodium borate, ethylenediamine tetraacetic acid, formaldehyde and Triton-X-100 in water.

13. The method in accordance with claim 10 wherein said bacteria in said sub-layers are detected by transferring said sub-layers to a microscope slide and observing said fluorescence emission of said ethidium bromide with a microscope.

14. The method in accordance with claim 10 wherein said bacteria in said sub-layers are detected by suspending said sub-layers in saline and observing said fluorescence emission of said ethidium bromide with a fluorescence activated flow cytometer.

15. The method in accordance with claim 10 wherein said bacteria in said sub-layers are detected by observing said fluorescence emission of said ethidium bromide directly in said microhematocrit tube with a microscope.

16. A method for the assessment of phagocytic activity comprising the steps of:
   (a) adding bacteria and an anticoagulant to a whole blood sample to provide a mixture;
   (b) incubating said mixture;
   (c) treating said mixture with a staining buffer and a fluorescent dye which selectively stains bacteria in the presence of blood components;
   (d) drawing said mixture into a hematocrit tube containing a float;
   (e) centrifuging said mixture, whereby a buffy coat is formed, and whereby the bacteria are concentrated in the buffy coat sublayer and the buffy coat expanded by said float, and separated into sub-layers;
   (f) examining said sub-layers of said buffy coat for the presence of bacteria by observing fluorescence emission of said sub-layers, and
   (g) determining the extent the phagocytosis by comparing the intensities of said fluorescence emission of said sub-layers.

17. The method in accordance to claim 16 wherein said fluorescent dye is ethidium bromide.

* * * * *